(12) United States Patent
Lee et al.

(10) Patent No.: US 12,383,237 B2
(45) Date of Patent: Aug. 12, 2025

(54) ULTRASOUND DIAGNOSTIC DEVICE AND METHOD FOR EXTRACTING CHARACTERISTIC POINTS FROM ACQUIRED ULTRASOUND IMAGE DATA USING A NEURAL NETWORK

(71) Applicant: ALPINION MEDICAL SYSTEMS CO., LTD., Hwaseong-si (KR)

(72) Inventors: Eun Gyu Lee, Daejeon (KR); Chul Hee Yun, Anyang-si (KR)

(73) Assignee: ALPINION MEDICAL SYSTEMS CO., LTD., Hwaseong-si (KR)

( * ) Notice: Subject to any disclaimer, the term of this patent is extended or adjusted under 35 U.S.C. 154(b) by 144 days.

(21) Appl. No.: 18/039,383

(22) PCT Filed: Nov. 9, 2021

(86) PCT No.: PCT/KR2021/016173
§ 371 (c)(1),
(2) Date: May 30, 2023

(87) PCT Pub. No.: WO2022/124591
PCT Pub. Date: Jun. 16, 2022

(65) Prior Publication Data
US 2023/0414202 A1    Dec. 28, 2023

(30) Foreign Application Priority Data
Dec. 11, 2020    (KR) .................... 10-2020-0173175

(51) Int. Cl.
*A61B 8/00*    (2006.01)
*A61B 8/08*    (2006.01)

(52) U.S. Cl.
CPC .......... *A61B 8/5223* (2013.01); *A61B 8/0866* (2013.01); *A61B 8/5207* (2013.01); *A61B 8/5269* (2013.01)

(58) Field of Classification Search
CPC .............. A61B 8/0866; A61B 5/7267; G06T 2207/20081; G06T 2207/20084
See application file for complete search history.

(56) References Cited

U.S. PATENT DOCUMENTS

| 7,783,095 B2 | 8/2010 | Carneiro et al. |
| 8,848,994 B2 | 9/2014 | Lee et al. |

(Continued)

FOREIGN PATENT DOCUMENTS

| EP | 3510937 A1 * | 7/2019 | ............... A61B 8/08 |
| EP | 3513731 A1 * | 7/2019 | ........... A61B 8/0866 |

(Continued)

OTHER PUBLICATIONS

JP-2020039645-A (Year: 2020).*

(Continued)

*Primary Examiner* — Jeffrey G Hoekstra
*Assistant Examiner* — Nyrobi Celestine
(74) *Attorney, Agent, or Firm* — NSIP Law

(57) ABSTRACT

Disclosed are a medical indicator measuring method and an ultrasound diagnostic device therefor. The medical indicator measuring method according to an embodiment includes the steps of: an ultrasound diagnostic device acquiring ultrasound image data, extracting characteristic points from the acquired ultrasound image data, generating figure information configured from the extracted characteristic points, determining an anatomical structure from the generated figure information, and measuring a medical indicator on the basis of the determined anatomical structure.

17 Claims, 6 Drawing Sheets

(56) References Cited

U.S. PATENT DOCUMENTS

| | | | |
|---|---|---|---|
| 9,122,959 B2 | 9/2015 | Zhou et al. | |
| 9,881,125 B2 | 1/2018 | Jung et al. | |
| 10,426,442 B1* | 10/2019 | Schnorr | A61B 8/5223 |
| 2007/0081705 A1* | 4/2007 | Carneiro | G06F 18/2321 |
| | | | 382/128 |
| 2013/0173175 A1* | 7/2013 | Jung | A61B 8/0866 |
| | | | 702/19 |
| 2013/0177223 A1* | 7/2013 | Lee | G06T 7/0012 |
| | | | 382/128 |
| 2014/0328527 A1 | 11/2014 | Zhou et al. | |
| 2015/0272541 A1 | 10/2015 | Hyuga | |
| 2016/0081663 A1* | 3/2016 | Chen | G06T 7/62 |
| | | | 600/407 |
| 2017/0296149 A1* | 10/2017 | Kobayashi | A61B 8/5223 |
| 2018/0140282 A1* | 5/2018 | Toyomura | G06V 10/82 |
| 2019/0000424 A1* | 1/2019 | Samset | A61B 8/0866 |
| 2019/0183455 A1 | 6/2019 | Lorenz et al. | |
| 2019/0192114 A1* | 6/2019 | Mauldin, Jr. | A61B 8/085 |
| 2020/0170615 A1* | 6/2020 | Roundhill | A61B 8/469 |
| 2021/0077062 A1 | 3/2021 | Schadewaldt et al. | |
| 2021/0304408 A1* | 9/2021 | Chaganti | G06T 7/11 |

FOREIGN PATENT DOCUMENTS

| | | | | |
|---|---|---|---|---|
| EP | 3639751 A1 | * | 4/2020 | ........... A61B 8/0866 |
| JP | 2007-267979 A | | 10/2007 | |
| JP | 5243845 B2 | | 7/2013 | |
| JP | 2015-198907 A | | 11/2015 | |
| JP | 2016-67814 A | | 5/2016 | |
| JP | 2016-522708 A | | 8/2016 | |
| JP | 2020039645 A | * | 3/2020 | |
| JP | 2021-510595 A | | 4/2021 | |
| JP | 7075854 B2 | | 5/2022 | |
| KR | 10-2013-0080312 A | | 7/2013 | |
| KR | 10-2013-0082318 A | | 7/2013 | |
| WO | WO 2019/145147 A1 | | 8/2019 | |

OTHER PUBLICATIONS

Korean Office Action issued on Nov. 24, 2023, in counterpart Korean Patent Application No. 10-2020-0173175 (3 pages in Korean).

* cited by examiner

ULTRASOUND DIAGNOSTIC DEVICE AND METHOD FOR EXTRACTING CHARACTERISTIC POINTS FROM ACQUIRED ULTRASOUND IMAGE DATA USING A NEURAL NETWORK

CROSS REFERENCE TO RELATED APPLICATIONS

This application is a U.S. National Stage Application of International Application No. PCT/KR2021/016173, filed on Nov. 9, 2021, which claims the benefit under 35 USC 119(a) and 365(b) of Korean Patent Application No. 10-2020-0173175, filed on Dec. 11, 2020, in the Korean Intellectual Property Office, the entire disclosure of which is incorporated herein by reference for all purposes.

TECHNICAL FIELD

The present invention relates to diagnostic technology using ultrasound, and more particularly, to a technology for measuring medical indicators using ultrasound.

The present invention was supported by the National Research and Development Project having grant number: 1425140041, project number: S2492471, department name: The Ministry of Small and Medium Enterprises and Start-ups, research management institution: Korea Institute for Advancement of Technology, research project name: WC300 R&D, research name Development of Software Beamforming Ultrasound Diagnostic Apparatus Line Up, and research supervising institute: Alpinion Medical System Co., Ltd.

BACKGROUND ART

Various imaging apparatuses for imaging information on the tissue of a human body are used in many medical areas for the early diagnosis of various diseases or surgical operations. Some examples of such medical imaging apparatuses are ultrasonic diagnostic apparatuses, computed tomography (CT) apparatuses, and magnetic resonance imaging (MRI) apparatuses.

Ultrasound diagnostic apparatuses emit an ultrasound signal generated by an ultrasound probe toward an object and receive information regarding an echo signal reflected from the object, thereby obtaining an image of a part inside the object. In particular. In particular, ultrasound diagnostic apparatuses are used for medical purposes including observing an internal area of an object, detecting foreign substances, assessing injuries, and the like. Such ultrasound diagnostic apparatuses provide high stability, display images in real time, and are safe due to no radiation exposure, compared to X-ray apparatuses. Therefore, ultrasound diagnostic apparatuses are widely used together with other types of imaging diagnostic apparatuses.

A method of emitting an ultrasound signal to an object through an ultrasound probe, measuring a size of a body part in an ultrasound image obtained using an ultrasound echo signal reflected from the object, and predicting a medical indicator is widely used. Semantic segmentation technique is one of methods of measuring a size of a body part. This technique is to segment objects in an image into meaningful units.

DISCLOSURE

Technical Problem

According to an embodiment, a medical indicator measuring method, which can more accurately, easily and automatically measure medical indicators, and an ultrasound diagnostic device therefor are proposed.

Technical Solution

A medical indicator measuring method according to an embodiment includes the steps of: an ultrasound diagnostic device acquiring ultrasound image data, extracting characteristic points from the acquired ultrasound image data, generating figure information configured from the extracted characteristic points, determining an anatomical structure from the generated figure information, and measuring a medical indicator on the basis of the determined anatomical structure.

In the step of extracting the characteristic points, a greater number of points than the minimum number of points required to construct a figure may be extracted.

In the step of extracting the characteristic points, points on a circumference forming an ellipse may be extracted, points on a circumference forming a circle may be extracted, both endpoints forming a line segment may be extracted, and each vertex forming a polygon may be extracted.

The extracting of the characteristic points may include the steps of: learning original image data together with image data of interest extracted from the original image data, extracting a first characteristic point of an object of interest from the original image data, generating image data of interest by transforming the original image data using the extracted first characteristic point, extracting a final characteristic point from the generated image data of interest, and inversely transforming coordinates of the final characteristic point to match the original image data.

In the step of learning, the learning may be performed using a structure in which a convolution layer of a neural network and a nonlinear function are repeatedly stacked on top of each other.

In the step of learning, loss of information caused by reducing an output size may be prevented by using padding of the neural network.

In the step of learning, the learning may be performed through a network structure connecting multi-resolution streams in parallel for repetitive exchange of resolution information between a first resolution frame and a second resolution frame.

In the step of generating the figure information, a zero-dimensional figure consisting of a point, a one-dimensional figure consisting of a straight line or a curve, or a two-dimensional figure consisting of an ellipse, a circle, or a polygon may be generated.

In the step of generating the figure information, basic figure information together with candidate figure information replaceable to the basic figure information may be generated.

In the step of generating the figure information, scores may be assigned to the extracted characteristic points, and the figure information may be generated using the characteristic points with scores higher than or equal to a preset reference.

In the step of generating the figure information, a relationship between the characteristic points may be configured using geometrical properties of a figure to be generated, and correction may be performed to remove outliers through the relationship between the characteristic points.

In the step of generating the figure information, the figure information may be corrected by retrieving at least one of another current parameter measurement value completely measured and a measurement result of the other fetus of twins from fetal biometric information pre-stored and accumulated.

In the step of generating the figure information, the figure information may be corrected by selecting the characteristic point through a user input of an operation signal for the generated figure information.

In the step of determining the anatomical structure, a head may be determined from an ellipse, an abdomen may be determined from a circle, and femur or humerus may be determined from a line segment or a quadrangle, and in the step of measuring the medical indicator, a head size may be measured using circumference points on the ellipse, an abdominal circumference may be measured using circumference points on the circle, and a length of the femur or humerus may be measured using both endpoints forming the line segment or four corners forming the quadrangle.

In the step of measuring the medical indicator, the medical indicator may be measured by taking into consideration the fetal biometric data related to pregnancy information regarding a patient among the pre-stored and accumulated fetal biometric data together.

The medical indicator measuring method may further include at least one of the steps of: distinguishably displaying the generated figure information as identifiable visual information on the ultrasound image data and displaying the measured medical indicator as numerical information on the figure of the ultrasound image data.

An ultrasound diagnostic device according to another embodiment may include an ultrasound probe configured to emit an ultrasound signal to an object and receive a reflected wave signal from the object, an image processing unit configured to generate ultrasound image data using the reflected wave signal of the ultrasound probe, a point extracting unit configured to extract characteristic points from the generated ultrasound image data, a figure generating unit configured to generate figure information configured from the extracted characteristic points, a structure determining unit configured to determine an anatomical structure from the generated figure information, an indicator measuring unit configured to measure a medical indicator on the basis of the determined anatomical structure, and an output unit configured to output a medical indicator measurement result.

Advantageous Effects

According to a medical indicator measuring method and an ultrasound diagnostic device therefor in accordance with an embodiment, it is possible to more accurately, easily, and automatically measure a medical indicator compared to a semantic segmentation technique.

MODES OF THE INVENTION

Figure 1:
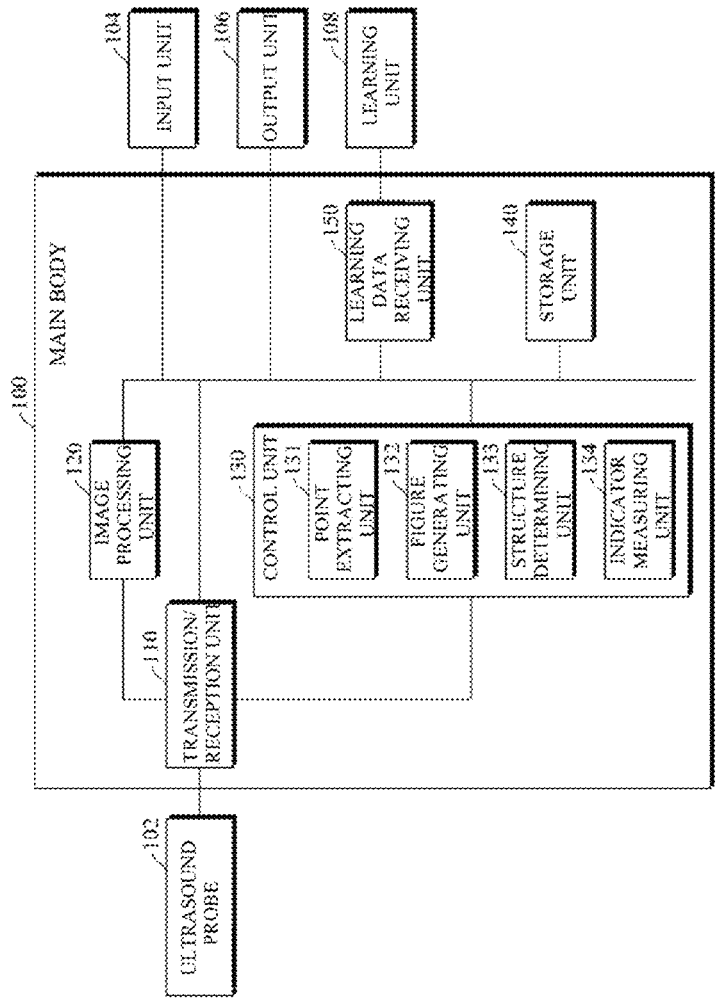
FIG. 1 is a diagram illustrating the configuration of an ultrasound diagnostic device according to an embodiment of the present invention.

The advantages and features of the present invention and the manner of achieving the advantages and features will become apparent with reference to embodiments described in detail below together with the accompanying drawings. However, the present invention may be implemented in many different forms and should not be construed as being limited to the embodiments set forth herein, and the embodiments are provided such that this disclosure will be thorough and complete and will fully convey the scope of the present invention to those skilled in the art, and the present invention is defined only by the scope of the appended claims. The same reference numerals refer to the same components throughout this disclosure.

In the following description of the embodiments of the present invention, if a detailed description of related known functions or configurations is determined to unnecessarily obscure the gist of the present invention, the detailed description thereof will be omitted herein. The terms described below are defined in consideration of the functions in the embodiments of the present invention, and these terms may be varied according to the intent or custom of a user or an operator. Therefore, the definitions of the terms used herein should follow contexts disclosed herein.

Combinations of each block of the accompanying block diagrams and each step of the accompanying flowcharts may be performed by computer program instructions (an execution engine), and these computer program instructions may be embedded in a processor of a general-purpose computer, a special purpose computer, or other programmable data processing equipment. Thus, these computer program instructions, which are executed through a processor of a computer or other programmable data processing equipment, produce tools for performing a function described in each block of the block diagrams or in each step of the flowcharts.

These computer program instructions may also be stored in a computer usable or readable memory which can be oriented toward a computer or other programmable data processing equipment so as to implement the function in a particular manner Therefore, the computer program instructions stored in the computer usable or readable memory may produce an article of manufacture containing an instruction tool for performing the function described in each block of the block diagrams or in each step of the flowcharts.

Further, the computer program instructions can also be mounted on a computer or other programmable data processing equipment. Therefore, the computer program instructions which serve to operate a computer or other programmable data processing equipment by performing a series of operation steps on the computer or the other programmable data processing equipment to produce a computer-implemented process may also provide steps for executing the functions described in each block of the block diagrams and in each step of the flowcharts.

Further, each block or each step may represent a module, a segment, or a part of a code, which includes one or more executable instructions for performing specified logical functions, and it should be noted that, in some alternative embodiments, the functions described in the blocks or steps may occur out of sequence. For example, two blocks or steps shown in succession may in fact be substantially executed at the same time, and the two blocks or steps may also be executed in the reverse order of the corresponding function as necessary.

Hereinafter, embodiments of the present invention will be described in detail with reference to the accompanying drawings. However, the present invention may be realized in various forms, and the scope of the present invention is not limited to such embodiments. The embodiments of the present invention are provided to aid those skilled in the art in the explanation and the understanding of the present invention.

FIG. 1 is a diagram illustrating the configuration of an ultrasound diagnostic device according to an embodiment of the present invention.

Referring to FIG. 1, the ultrasound diagnostic device includes an ultrasound probe 102, a main body 100, an input unit 104, an output unit 106, and a learning unit 108. The ultrasound probe 102, the input unit 104, and the output unit 106 are communicatively connected to the main body 100.

The ultrasound probe 102 includes a plurality of piezoelectric resonators, and the plurality of piezoelectric resonators generate ultrasonic waves based on a driving signal supplied from a transmission/reception unit 110 of the main body 100. Further, the ultrasound probe 102 receives reflected waves from an object and converts the reflected wave into an electrical signal. That is, the ultrasound probe 102 emits ultrasonic waves to the object and receives reflected waves from the object. The ultrasound probe 102 is detachably connected to the main body 100. The object may be a fetus of a pregnant woman, but is not limited thereto, such that the object may be any patient.

The input unit 104 is implemented by a track ball for performing settings for a predetermined position (e.g., a position of a tissue shape, a region of interest, a region other than the region of interest, etc.) a mouse, a keyboard, a touch pad for performing an input operation by touching an operation surface, a screen which is an integration of a display screen and a touch pad, a non-contact input circuit using an optical sensor, an audio input circuit, and the like. The input unit 104 is connected to a control unit 130 to be described below, converts an input operation signal received from a user into an electrical signal, and outputs the electrical signal to the control unit 130.

The output unit 106 displays a graphical user interface (GUI) for the user of the ultrasound diagnostic device to input various setting requests using the input unit 104, or displays ultrasound image data and the like generated in the main body 100. In addition, the output unit 106 displays various messages or information to inform the user of a processing status or processing result of the main body 100. Also, the output unit 106 may include a speaker and output audio. The output unit 106 may display a medical indicator measurement result generated through the control unit 140 on a screen. The medical indicator may be, for example, a fetal indicator. The fetal indicator includes the abdomen, head, femur, humerus, and the like of a fetus. However, the medical indicator is not limited to the fetal indicator, and may be any body organ of the object. For example, the medical indicator may be a pelvis or the like.

The output unit 106 may distinguishably display figure information generated through the control unit 130 as identifiable visual information (e.g., color) on the ultrasound image data. The output unit 106 may display the measured medical indicator as numerical information on the figure of the ultrasound image data.

The medical indicator measured through the control unit 130 may be displayed as numerical information on the ultrasound image data.

The learning unit 108 performs learning for the ultrasound image data using a neural network. In this case, at least one of components constituting the control unit 130, i.e., a point extracting unit 131, a figure generating unit 132, a structure determining unit 133, and an indicator measuring unit 134 may use learning data. The learning unit 108 may be in the form of a server connected to the main body 100 through a network, or may be located inside the main body 100. The learning unit 108 may learn original image data together with image data of interest extracted from the original image data.

The main body 100 is a device that generate ultrasound image data on the basis of a reflected wave signal received by the ultrasound probe 102. The main body 100 according to an embodiment includes a transmission/reception unit 110, an image processing unit 120, the control unit 130, a storage unit 140, and a learning data receiving unit 150.

The transmission/reception unit 110 provides a driving signal to the ultrasound probe 102 and repeatedly generates pulses for forming transmission ultrasound waves at a predetermined frequency. Also, the transmission/reception unit 110 converges ultrasound waves generated from the ultrasound probe 102 by using beamforming. The transmission/reception unit 110 may include a preamplifier, an analog-to-digital (A/D) converter, a reception delaying unit, a summing unit, and the like, and may generate reflected wave data by performing various processing on an echo signal received by the ultrasound probe 102. Various forms may be selected as the form of the output signal from the transmission/reception unit 110, such as a signal including phase information, which is called a radio frequency (RF) signal, or amplitude information after envelope detection.

The image processing unit 102 receives the reflected wave data from the transmission/reception unit 110 and generates ultrasound image data regarding the fetus. In this case, the image processing unit 120 performs logarithmic amplification, envelope detection processing, or the like to generate the ultrasound image data.

The storage unit 140 stores image data generated through the image processing unit 120 or the control unit 130.

The controller 130 controls each component of the ultrasound diagnostic device. For example, the control unit 130 controls processing of the transmission/reception unit 110 and the image processing unit 120 based on various setting requests input from the user through the input unit 130 or various control programs and various data read from the storage unit 140. In addition, the control unit 130 controls the ultrasound image data stored in the storage unit 140 to be displayed through the output unit 106.

The control unit 130 according to an embodiment includes the point extracting unit 131, the figure generating unit 132, the structure determining unit 133, and the indicator measuring unit 134.

The point extracting unit 131 extracts characteristic points from the ultrasound image data generated through the image processing unit 120. The characteristic points may include characteristic points defining a boundary, characteristic points showing the overall shape, a difference in pixel brightness values, and the like. For example, points on a circumference forming an ellipse may be extracted, points on a circumference forming a circle may be extracted, both endpoints forming a line segment may be extracted, and each vertex forming a polygon may be extracted. The polygon may include a triangle, a quadrangle, a pentagon, etc. In the case of an ellipse, focal points may be further extracted, and in the case of a circle, the center point may be further extracted to increase the accuracy.

The figure generating unit 132 generates figure information configured with the characteristic points extracted through the point extracting unit 131. For example, a zero-dimensional figure consisting of a point, a one-dimensional figure consisting of a straight line or curve, or a two-dimensional figure consisting of an ellipse, a circle, or a polygon.

The structure determining unit 133 determines an anatomical structure from the figure information generated through the figure generating unit 132. For example, the anatomical structure may include the abdomen, head, bone, and the like of the fetus. Examples of the bone may include femur, humerus, and the like. In determination of the anatomical structure, for example, the fetal abdomen is determined from a circle, the fetal head may be determined from an ellipse, and the fetal bone is determined from a line segment or a quadrangle.

The indicator measuring unit 134 measures a medical indicator on the basis of the anatomical structure determined through the structure determining unit 133. For example, the head circumference is measured from the circumference of the ellipse, the abdominal circumference is measured from the circumference of the circle, and the femur length is measured from the length of the line segment or quadrangle.

It will be referred to as a key-point detection technique in that the control unit 130 extracts points forming a figure, generates a figure using the extracted characteristic points, and then measure an indicator of the fetus from the generated figure. A more detailed embodiment with respect to the key-point detection technique will be described below with reference to FIG. 2.

The learning data receiving unit 150 receives learning data from the learning unit 108 and transmits the training data to the control unit 130. For example, the original image data and the image data of interest learned through the learning unit 108 may be provided to the point extracting unit 131 of the control unit 130.

Figure 2:
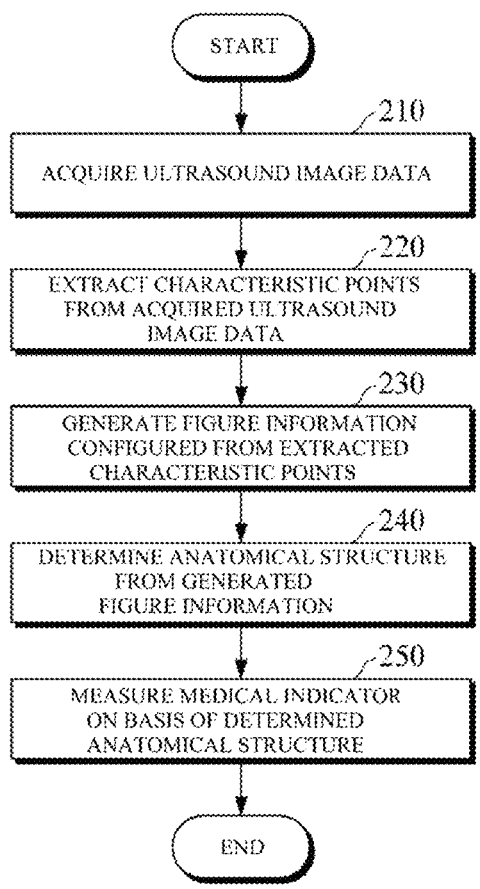
FIG. 2 is a flowchart illustrating a medical indicator measuring method using an ultrasound diagnostic device according to an embodiment of the present invention.

FIG. 2 is a flowchart illustrating a medical indicator measuring method using an ultrasound diagnostic device according to an embodiment of the present invention.

Referring to FIG. 2, the ultrasound diagnostic device acquires ultrasound image data of a fetus (210).

Then, the ultrasound diagnostic device extracts characteristic points from the acquired ultrasound image data (220). The characteristic points may include characteristic points defining a boundary, characteristic points showing the overall shape, a difference in pixel brightness values, and the like.

The step (220) of extracting the characteristic points may include the steps of learning, extracting a first characteristic point, transforming, and extracting a second characteristic point. For example, the ultrasound diagnostic device learns original image data together with image data of interest extracted from the original image data through the step of training. The original image data is an original image captured by equipment, and the image data of interest is an image obtained by extracting (e.g., cropping) a region of interest, in which an object of interest is determined to be present, from the original image data. The ultrasound diagnostic device generates the original image data and the image data of interest based on labels of the image data and performs learning on all generated image data.

Before the characteristic point extraction, an object location may be searched from the original image data and the image may be cropped based on the found object location. If the characteristic points are extracted by first searching for the object location and then inputting the original image data cropped based on the object location, the accuracy is greatly improved. The image size may be resized to an input size (e.g., 256×256) of a network.

Subsequently, the ultrasound diagnostic device extracts a first characteristic point of the object of interest from the original image data through the step of extracting the first characteristic point.

Then, the ultrasound diagnostic device generate the image data of interest by transforming the original image data using the extracted first characteristic point through the step of transforming. In this case, the transforming may include rotation, warping, magnification, and the like.

Thereafter, the ultrasound diagnostic device extracts a final characteristic point from the generated image data of interest and inversely transforms the coordinates of the final characteristic point to match the original image data.

According to the above process, there are data augmentation effects through learning. False detection may be corrected through the steps of learning, extracting the first characteristic point, and extracting the second characteristic point. Target data standardization effects may be achieved through transformation, such as image warping or the like. Pixel accuracy may be improved through transformation, such as image magnification.

In the step (220) of extracting the characteristic points, a greater number of points than the minimum number required to construct a figure may be extracted. This is to construct a figure intended to be made even when an object in the ultrasound image is incomplete and thus a key point cannot be detected. Therefore, more points than information constituting the figure are extracted. For example, in the case of an ellipse, although four points are required to form the ellipse, 16 points may be extracted to increase accuracy.

In the case of an ellipse, the circumference of the ellipse is defined as an outline of an object. Five or more points (e.g., 16 points) are extracted along the circumference of the ellipse. In the case of a rectangle, four points corresponding to the corners are extracted from the boundary of the rectangle containing an object. However, when the object is bent in the form of a curve, rectangles at both ends of the object, rather than the rectangle containing the entire object, may be defined as effective rectangles, and points corresponding to the effective rectangles are extracted. Further, points corresponding to a lower end portion of the actual object, along with the four vertex portions, may be further extracted.

In the step (220) of extracting the characteristic points, the ultrasound diagnostic device may extract points on a circumference forming an ellipse (additionally, the focal point), extract points on a circumference forming a circle (additionally, the center point), extract both endpoints forming a line segment, and extract each vertex forming a polygon. The polygon may include a triangle, a quadrangle, a pentagon, etc.

Then, the ultrasound diagnostic device generates figure information configured with the extracted characteristic points (230).

In the step (230) of generating the figure information, the ultrasound diagnostic device may generate a zero-dimensional figure consisting of a point, a one-dimensional figure consisting of a straight line or a curve, or a two-dimensional figure consisting of an ellipse, a circle, or a polygon.

In the step (230) of generating the figure information, the ultrasound diagnostic device may generate basic figure information together with candidate figure information replaceable to the basic figure information. For example, a figure consisting of both upper end points of the leg bone is set as basic figure information, and a figure which consists of both lower end points of the leg bone and is similar in length is set as candidate figure information.

In the step (230) of generating the figure information, the ultrasound diagnostic device may assign scores to the extracted characteristic points and generate the figure information using the characteristic points with scores higher than or equal to a preset reference.

In the step (230) of generating the figure information, the ultrasound diagnostic device may further include a step of performing correction based on characteristics of a figure to be created when generating the figure information using the extracted characteristic points. Since the extracted characteristic points are components of a certain figure, a relationship between the characteristic points may be configured using geometrical properties of the figure to be created and outliers may be removed in advance through the relationship between the characteristic points. For example, in the case of a circle, outliers may be removed using the distance relationship between the center point and each characteristic point. In the case of an ellipse, outliers may be removed using distance information of the focal point, the minor axis, and the major axis. Since a distance d from each point forming the ellipse to the center point is defined as $a/2 \leq d \leq b/2$ (here, a is the minor axis and b is the major axis), a point that does not satisfy the relationship may be determined to be an outlier and removed.

In the step (230) of generating the figure information, the figure information may be corrected by retrieving at least one of another current parameter measurement value completely measured and a measurement result of the other fetus of twins from fetal biometric information pre-stored and accumulated. In another example, the figure information may be corrected by selecting a point through a user input of an operation signal for the generated figure information.

In the step (230) of generating the figure information, the ultrasound diagnostic device may distinguishably display the generated figure information as identifiable visual information on the ultrasound image data.

Subsequently, the ultrasound diagnostic device determines an anatomical structure from the generated figure information (240), and measures a medical indicator on a basis of the determined anatomical structure (250).

In the step (250) of measuring the medical indicator, the ultrasound diagnostic device may measure fetal head size using points on a circumference forming an ellipse (additionally, the focal point), measure fetal abdominal circumference using points on a circumference forming a circle (additionally, the center point), and measure the length of a fetal bone using both endpoints forming a line segment or four corners forming a quadrangle.

In the step (250) of measuring the medical indicator, the ultrasound diagnostic device may measure the medical indicator by taking into consideration the fetal biometric data related to pregnancy information regarding a patient among the prestored and accumulated fetal biometric data together. The pregnancy information includes the last menstrual period (LMP) or date of conception (DOC) of the patient.

Furthermore, the ultrasound diagnostic device may perform learning for the ultrasound image data using a neural network. In this case, learning data may be used in at least one of the steps of extracting the characteristic points (220), generating the figure information (230), determining the anatomical structure (240), and measuring the medical indicator (250).

In the step of learning, the ultrasound diagnostic device may perform learning by using a structure in which a convolution layer of a neural network and a nonlinear activation function (Relu) are repeatedly stacked on top of each other.

In the step of learning, the ultrasound diagnostic device may use padding of the neural network to prevent loss of information caused by reducing an output size and maintain the resolution of an original layer constantly.

In the step of learning, the ultrasound diagnostic device may perform learning through a network structure connecting multi-resolution streams in parallel for repetitive exchange of resolution information between a first resolution frame and a second resolution frame. The first resolution frame may be a high-resolution frame, and the second resolution frame may be a low-resolution frame. In this case, resolution information may be repeatedly exchanged between the high resolution frame and the low resolution frame.

The ultrasound diagnostic device may display the measured medical indicator as numerical information on the figure of the ultrasound image data.

Figure 3:
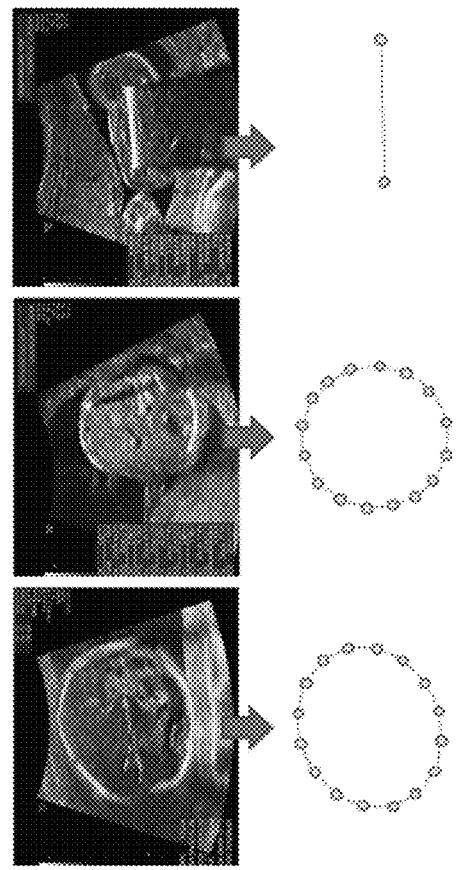
FIG. 3 is a diagram illustrating an example of extracting characteristic points from ultrasound image data according to an embodiment of the present invention.

FIG. 3 is a diagram illustrating an example of extracting characteristic points from ultrasound image data according to an embodiment of the present invention.

Referring to FIG. 3, the ultrasound diagnostic device may extract points on a circumference forming an ellipse to measure fetal head size. In FIG. 3, 16 points forming an ellipse are extracted. In addition, the ultrasound diagnostic device may extract points on a circumference forming a circle to measure the fetal abdominal circumference. In FIG. 3, 16 points forming a circle are extracted. In another example, both endpoints forming a line segment may be extracted to measure the length of a bone.

Figure 4:
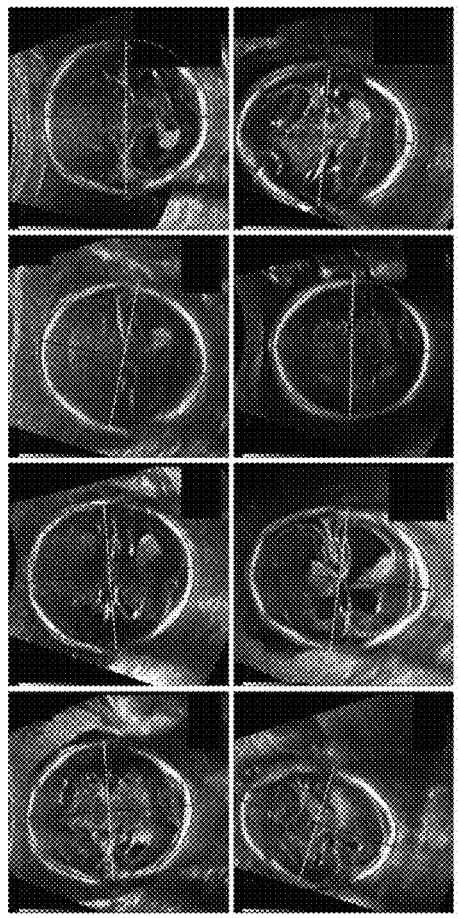
FIG. 4 shows illustrations showing screens displayed when measuring fetal head size using a key-point detection technique according to an embodiment of the present invention.

FIG. 4 shows illustrations showing screens displayed when measuring fetal head size using a key-point detection technique according to an embodiment of the present invention.

Referring to FIG. 4, the ultrasound diagnostic device extracts points on a circumference forming an ellipse from ultrasound image data, determines a head from the ellipse, and measures fetal head size using the points on the circumference forming the ellipse (additionally, the focal point).

At this time, the circumference of the ellipse and the length of the horizontal axis and the length of the vertical axis in the ellipse may be distinguishably displayed as identifiable visual information (e.g., color). In addition, the measurement value of the fetal abdominal circumference including the length of the horizontal axis and the length of the vertical axis may be displayed on the horizontal axis and the vertical axis.

Figure 5:
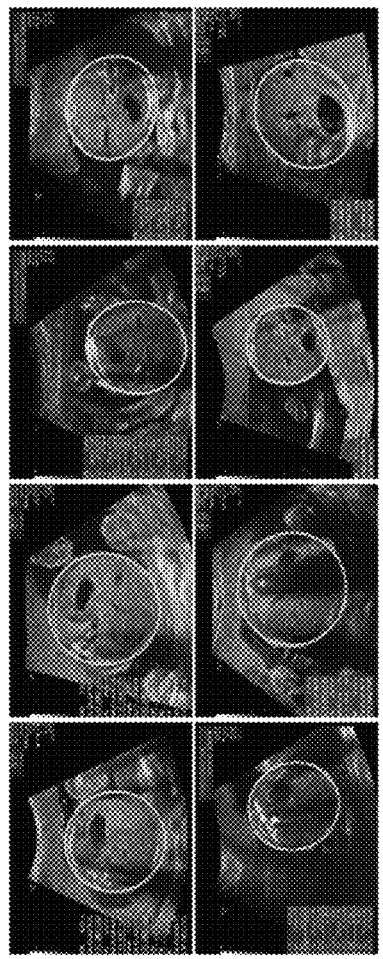
FIG. 5 shows illustrations showing screens displayed when measuring fetal abdominal circumference using a key-point detection technique according to an embodiment of the present invention.

FIG. 5 shows illustrations showing screens displayed when measuring fetal abdominal circumference using a key-point detection technique according to an embodiment of the present invention.

Referring to FIG. 5, points on a circumference forming a circle are extracted from ultrasound image data, the fetal abdomen is determined from the circle, and fetal abdominal circumference is measured using circumferential points and a center point forming a circle.

In this case, the circumference of the center may be distinguishably displayed as identifiable visual information (e.g., color). In addition, the measurement value of the fetal abdominal circumference may be displayed on the circle.

Figure 6:
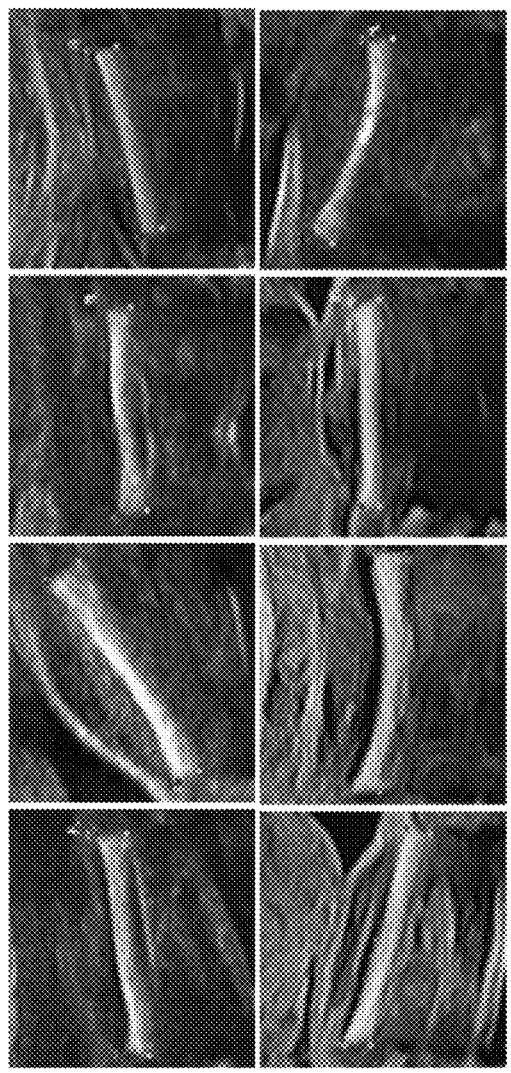
FIG. 6 shows illustrations showing screens displayed when measuring the length of a fetal bone using a key-point detection technique according to an embodiment of the present invention.

FIG. 6 shows illustrations showing screens displayed when measuring the length of a fetal bone using a key-point detection technique according to an embodiment of the present invention.

Referring to FIG. 6, both end points forming a line segment are extracted from ultrasound image data, and the length of a fetal bone is measured using both endpoints forming the line segment.

In this case, both endpoints of the line segment and the line segment connecting the two endpoints may be distinguishably displayed as identifiable visual information (e.g., color). In addition, the measurement value of the fetal bone may be displayed on a bone.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

The invention claimed is:

1. A medical indicator measuring method performed by an ultrasound diagnostic device, comprising:
acquiring ultrasound image data;
extracting characteristic points for generating figure information from the acquired ultrasound image data using a neural network, wherein the characteristic points include at least one of characteristic points defining a boundary and characteristic points showing the overall shape in the acquired ultrasound image data, the neural network receiving the ultrasound image data as an input and outputting the characteristic points;
generating figure information by connecting the extracted characteristic points into a geometric figure;
determining an anatomical structure from the generated figure information; and
measuring a medical indicator on the basis of the determined anatomical structure, the medical indicator being a geometric measurement of the connected extracted points of the determined anatomical structure, wherein the medical indicator includes at least one of a length, a perimeter, or an area of the geometric figure.

2. The medical indicator measuring method of claim 1, wherein in extracting the characteristic points, a greater number of points than the minimum number of at least two points required to construct a figure are extracted.

3. The medical indicator measuring method of claim 1, wherein in extracting the characteristic points, points on a circumference forming an ellipse are be extracted, points on a circumference forming a circle are extracted, both endpoints forming a line segment are extracted, and each vertex forming a polygon are extracted.

4. The medical indicator measuring method of claim 1, wherein the extracting of the characteristic points comprises:
learning original image data together with image data of interest extracted from the original image data;
extracting a first characteristic point of an object of interest from the original image data using the neural network, the neural network receiving the ultrasound image data as an input and outputting the characteristic points;
generating image data of interest by transforming the original image data using the extracted first characteristic point;
extracting a final characteristic point from the generated image data of interest; and
inversely transforming the image data, including coordinates of the final characteristic point to match the original image data.

5. The medical indicator measuring method of claim 4, wherein the learning is a training phase of the neural network and the learning is performed using a structure in which a convolution layer of the neural network and a nonlinear function are repeatedly stacked on top of each other.

6. The medical indicator measuring method of claim 4, wherein in the learning, loss of image data information caused by reducing an output size is prevented by using padding of the neural network.

7. The medical indicator measuring method of claim 4, wherein the learning is a training phase of the neural network and the learning is performed through a network structure connecting multi-resolution streams in parallel for repetitive exchange of resolution information between a first resolution frame and a second resolution frame, wherein the first resolution frame and the second resolution frame are frames generated from the image data.

8. The medical indicator measuring method of claim 1, wherein in generating the figure information, a zero-dimensional figure consisting of a point, a one-dimensional figure consisting of a straight line or a curve, or a two-dimensional figure consisting of an ellipse, a circle, or a polygon is generated.

9. The medical indicator measuring method of claim 1, wherein in generating the figure information, at least two sets of figures, comprising basic figure information and candidate figure information replaceable to the basic figure information, are generated.

10. The medical indicator measuring method of claim 1, wherein in generating the figure information, scores are assigned to the extracted characteristic points, and the figure information is generated using the characteristic points with scores higher than or equal to a preset reference score of points.

11. The medical indicator measuring method of claim 1, wherein in generating the figure information, a relationship between the characteristic points, wherein the relationship refers to connecting the characteristic points into the figure, is configured using geometrical properties of the figure to be generated and correction is performed to remove outliers through the relationship between the characteristic points.

12. The medical indicator measuring method of claim 1, wherein in generating the figure information, the figure information is corrected by retrieving at least one of parameter measurement value, which is a geometric measurement of objects in an ultrasound image, fetal biometric information pre-stored and accumulated.

13. The medical indicator measuring method of claim 1, wherein in generating the figure information, the figure information is corrected by selecting the characteristic point through a user input of an operation signal for the generated figure information through a user interface.

14. The medical indicator measuring method of claim 1, wherein in determining the anatomical structure, a head is determined from an ellipse, an abdomen may be determined from a circle, and femur or humerus is determined from a line segment or a quadrangle, and in measuring the medical indicator, a head size is measured using circumference points on the ellipse, an abdominal circumference is measured using circumference points on the circle, and a length of the femur or humerus is measured using both endpoints forming the line segment or four corners forming the quadrangle.

15. The medical indicator measuring method of claim 1, wherein in measuring the medical indicator, the medical indicator of a fetus is measured by taking into consideration the fetal biometric data related to pregnancy information regarding a patient among the pre-stored and accumulated fetal biometric data together.

16. The medical indicator measuring method of claim 1, further comprising at least one of:

distinguishably displaying the generated figure information as identifiable visual information on the ultrasound image data; and displaying the measured medical indicator as numerical information on the figure of the ultrasound image data.

17. An ultrasound diagnostic device comprising:

an ultrasound probe configured to emit an ultrasound signal to an object and receive a reflected wave signal from the object;

one or more processors configured to:

generate ultrasound image data using the reflected wave signal of the ultrasound probe;

extract characteristic points for generating figure information from the generated ultrasound image data using a neural network, wherein the characteristic points include at least of characteristic points defining a boundary and characteristic points showing the overall shape in the acquired ultrasound image data, the neural network receiving ultrasound image data as an input and outputting the characteristic points;

generate figured to generate figure information by connecting the extracted characteristic points into a geometric figure;

determine an anatomical structure from the generated figure information;

measure a medical indicator on the basis of the determined anatomical structure, the medical indicator being a geometric measurement of the connected extracted points of the determined anatomical structure, wherein the medical indicator includes at least one of a length, a perimeter, or an area of the geometric figure; and a display configured to output a medical indicator measurement result.

* * * * *